United States Patent [19]

Hawke

[11] Patent Number: 4,837,165
[45] Date of Patent: Jun. 6, 1989

[54] METHOD FOR SEQUENCING OF PEPTIDES BY CARBOXYL TERMINUS DEGRADATION

[75] Inventor: David H. Hawke, Azusa, Calif.

[73] Assignee: Beckman Research Institute, City of Hope, Duarte, Calif.

[21] Appl. No.: 186,667

[22] Filed: Apr. 20, 1988

Related U.S. Application Data

[63] Continuation of Ser. No. 780,264, Sep. 26, 1985, abandoned.

[51] Int. Cl.$^4$ ............................................. G01N 33/68
[52] U.S. Cl. ................................... 436/89; 530/345; 530/402
[58] Field of Search .................. 436/89, 161; 530/345, 530/402, 427

[56] References Cited

U.S. PATENT DOCUMENTS 4,065,412 12/1977 Dreyer ............................ 530/345 X

OTHER PUBLICATIONS

Edman, "Protein Sequence Determination", Edited by S. Needleman, Chapter 8, pp. 211–255, Spring-Verlog, N.Y., 1970.
Stark, Biochemistry, vol. 7, No. 5, pp. 1796–1807, 1968.
Cromwell et al., Biochemistry, vol. 8, No. 12, pp. 4735–4740, 1969.
Meuth et al., Biochemistry, vol. 21, No. 16, pp. 3750–3757, 1982.
Kricheldorf et al., Chemical Abstracts, vol. 79, Abstract No. 53835p, 1973.
Ram et al., Chemical Abstracts, vol. 99, Abstract No. 37638j, 1983.
Ram et al., Chemical Abstracts, vol. 99, Abstract No. 194571z, 1983.
Fokin et al., Chemical Abstracts, vol. 78, Abstract No. 158965p, 1973.
Fokin et al., Chemical Abstracts, vol. 77, Abstract No. 87794y, 1972.
Kodama et al., Chemical Abstracts, vol. 87, Abstract No. 87:68430s, 1976.

*Primary Examiner*—Robert J. Hill, Jr.
*Attorney, Agent, or Firm*—Edward S. Irons

[57] ABSTRACT

A peptide is sequenced from its carboxyl terminal by coupling with an isothiocyanate having a chemical formula $R_{(x)}Si(NCS)_y$ where $x=0-3$ and $y=1-4$. R may be alkyl or aryl. The coupling reaction is preferably conducted at a temperature range of 50°–90° C. for a period to approximately sixty (60) minutes or less. A weak acid anhydride, preferably a carboxylic acid anhydride, or a weak acid chloride, preferably a carboxylic acid chloride, may be mixed with the isothiocyanate. An organic base catalyst selected from a group consisting of tertiary amines including aromatic amines such as pyridine may also be utilized.

8 Claims, No Drawings

METHOD FOR SEQUENCING OF PEPTIDES BY CARBOXYL TERMINUS DEGRADATION

This is a continuation of application Ser. No. 780,264, filed Sept. 26, 1985, now abandoned.

This invention relates to a method of sequencing a peptide to separate in a stepwise manner the amino acids at the carboxyl terminal of the peptide for individual identification. The invention also relates to the materials used in such sequencing.

It is often desirable to sequence a peptide by isolating and identifying sequentially derivatives of the amino acids forming the peptide. For example, such sequencing is desirable in research to identify the order in which the amino acids are arranged in the peptides so that the peptides can be subsequently synthesized. Such knowledge can also enable the design of suitable probes to obtain gene sequences which in turn will enable production of the peptide using recombinant DNA technology. Such sequencing can thus lead to the development of materials which will combat diseases.

Methods are now in use for sequencing amino acids from the carboxyl terminal and the N-terminal of peptides. The methods of sequencing peptides from the N-terminal are relatively elegant in their ease of operation, reliability, sequencing speed, sensitivity and span of sequence determination. In contrast, the present methods of sequencing amino acids from the carboxyl terminals of peptides are not nearly as well developed. For example, not all of each amino acid in the sequence is cleaved from the peptide. As a result, the amount of peptide available for the cleavage of successive amino acids becomes progressively reduced. The identification of successive amino acids in the peptide sequence accordingly becomes increasingly difficult. This limits the number of amino acids capable of being sequenced and accurately identified in the peptide.

There are other serious disadvantages with the present method of sequencing amino acids from the carboxyl terminal of the peptides. For example, ionic thiocyanates are generally used to convert the peptides into an intermediate form, such as peptidyl thiohydantoin derivative, which can be processed to cleave the amino acids. Such thiocyanate reactants tend to be self reactive at ambient temperatures and quickly lose their ability to act upon the peptide. Furthermore, even when the thiocyanate is able to act upon the peptide, the reaction temperature has to be relatively high, such as in the order of 90° C., and the reaction time has to be relatively long.

The problems of sequencing amino acids from the carboxyl terminal of the peptides have been known for some time. A considerable effort has been made to develop methods of, and chemicals for, overcoming such problems. In spite of such efforts, the problems have still remained.

This invention provides methods of, and chemicals for, overcoming the problems specified above. In producing the peptidyl thiohydantoin derivative, the invention uses a chemical which is stable at room temperatures. Thus, such chemical can be stored for relatively long periods of time without losing its effectiveness. The chemical is effective in each step in producing a substantially complete conversion of the peptide to a peptidyl thiohydantoin derivative, thereby providing for substantially complete cleavage of the thiohydantoin derivative of the amino acid at each carboxyl position of the peptide. This facilitates the identification of the amino acid in each of the thiohydantoin derivatives and also provides for an increase in the number of the amino acids sequentially capable of being sensitively and reliably identified in a peptide. The invention is also effective in reducing the reaction temperatures and times for producing the peptidyl thiohydantoin derivative, thus reducing the experimental time required to achieve the desired information.

In the method constituting this invention, peptides at their carboxyl terminals are sequenced by applying to the peptides an isothiocyanate having a chemical formula $R_{(x)}Si(NCS)_y$ where $x=0-3$ and $y=1-4$. R may constitute an alkyl or an aryl substituent. This application of the isothiocyanate to the peptide preferably occurs in a temperature range of approximately 50°–90° C. for a period to approximately sixty (60) minutes or less.

A weak acid anhydride, preferably a carboxylic acid anhydride, or a weak acid chloride, preferably a carboxylic acid chloride, may be mixed with the isothiocyanate. A catalyst may also be included. The catalyst is an organic base and may be selected from a group consisting of tertiary amines including aromatic amines such as pyridine. A thiohydantoin substituent is thereby produced from the amino acid at the carboxyl terminal of the peptide. Excess reagents may then be removed by extraction with a suitable solvent. This removal is facilitated if the peptide is initially immobilized by fixation to a solid support or entrapment within a matrix or retentive material, such as polybrene.

The peptidyl thiohydantoin derivative may then be cleaved to separately provide a thiohydantoin derivative of the amino acid previously at the carboxyl terminal of the original peptide and a peptidyl residue. The process specified above may then be repeated to yield a peptidyl thiohydantoin derivative of the amino acid at the new carboxyl terminal of the peptidyl residue, and this peptidyl thiohydantoin derivative may be cleaved to separate the next amino acid in the sequence for identification. The amino acids sequentially separated from the carboxyl terminal of the peptide may be individually identified.

Equation 1 illustrates the formation of a peptidyl thiohydantoin derivative by reaction of a peptide with an isothiocyanate in acetic anhydride, in the presence of a catalyst, in one step of a method constituting this invention:

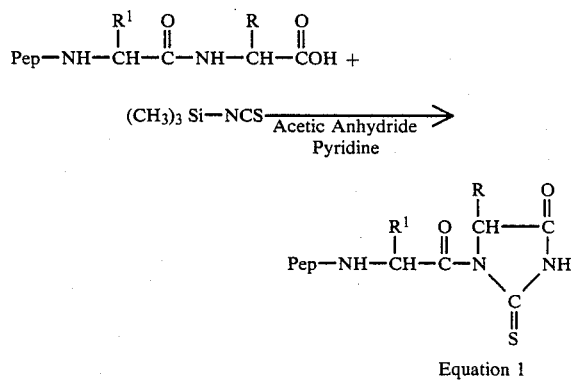

Equation 1

Equation 2 illustrates the cleavage of the peptidyl thiohydantoin derivative, as by hydrochloric acid, in another step of the method constituting this invention to yield a peptidyl residue and a thiohydantoin derivative of an amino acid previously at the carboxyl terminal of the initial peptide:

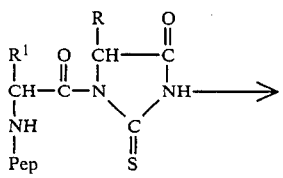

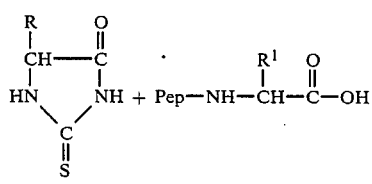

Equation 2

In one embodiment of the invention, a peptide is sequenced at its carboxyl terminal to separate the amino acids in the peptide so that the amino acids can be individually identified. The peptide can be quite large. For example, peptides with as many as fifty (50) amino acids or more can be sequenced sequentially to identify the amino acids sequentially.

The peptides are treated with an isothiocyanate. Preferably the isothiocyanate is trimethylsilyl isothiocyanate. However, the isothiocyanate can be defined as $R_xSi(NCS)_y$ where $x=0-3$ and $y=1-4$ and where R can be an alkyl, aryl, substituted alkyl, substituted aryl, or any combination of these. Trimethylsilyl isothiocyanate is advantageous because it is stable at ambient temperatures. As a result, it can be stored on a shelf for long periods of time without any significant deterioration. However, since trimethylsilyl isothiocyanate is reactive with water, it should be isolated from water or water vapor.

The treatment of the peptide with the isothiocyanate specified in the previous paragraph is facilitated by the inclusion of a weak acid anhydride or a weak acid chloride in the mixture. Acetic anhydride is preferred, although the use of acetyl choloride is also desirable.

The reaction of the peptide with the agent such as trimethylsilyl isothiocyanate is expedited by the inclusion of a catalyst such as pyridine in the mixture. The inclusion of the pyridine in the mixture helps to couple the peptide to the isothiocyanate. Preferably a concentration of pyridine of approximately two percent (2%) by volume in the mixture may be used. However, the amount of pyridine in the mixture may be used anywhere in the range to approximately eighty percent (80%) by volume in the mixture with beneficial results. Other catalysts such as dimethylaminopyridine, triethylamine and dimethyl ethylamine may also be used. All of these catalysts are organic bases. The catalyst may be selected from a group consisting of tertiary amines including amines such as pyridine.

In a typical experiment, 10 μl of peptide solution containing 2 to 20 nmoles of peptide was mixed with 50 μl of acetic anhydride. The mixture was heated for approximately 10 minutes, and then a large excess of the coupling reagent (5 μl of trimethylsilyl isothiocyante) was added. The resulting solution was 0.54M with respect to the coupling reagent. Peptide concentrations were respectively 31 μM and 310 μM (2 and 20 nmol).

The sample was vacuum dried and then dissolved in 50 μl of 12N hydrochloric acid. After approximately thirty (30) minutes at room temperature, the sample was again dried and then dissolved in water for high performance liquid chromatography (HPLC) analysis. Table 1 reports data from experiments utilizing bradykinin as a model peptide and the materials specified above.

TABLE 1

| nmole peptide | T (°C.) | t (min) | reagent | catalyst | note |
|---|---|---|---|---|---|
| 2 | 90 | 10 | TMS—NCS | DMAP | |
| 2 | 70 | 4 | TMS—NCS | DMAA | |
| " | " | 2 | " | Pyridine | |
| " | " | 2 | " | " | |
| " | " | 4 | " | " | |
| " | " | 4 | " | " | |
| " | " | 8 | " | " | |
| " | " | 8 | " | " | |
| " | " | 16 | " | " | |
| " | " | 16 | " | " | |
| 2 | 70 | 4 | TMS—NCS | none | |
| " | " | 4 | " | " | |
| " | " | 8 | " | " | |
| " | " | 8 | " | " | |
| " | " | 16 | " | " | |
| " | " | 16 | " | " | |
| " | " | 32 | " | " | |
| " | " | 32 | " | " | |
| 2 | 90 | 2 | TMS—NCS | none | |
| " | " | 2 | " | " | |
| " | " | 4 | " | " | |
| " | " | 4 | " | " | |
| " | " | 8 | " | " | |
| " | " | 8 | " | " | |
| 2 | 90 | 10 | TMS—NCS | Pyridine | |
| " | 50 | 15 | " | " | |
| " | " | 30 | " | " | |
| " | 90 | 30 | " | none | |
| " | " | 30 | " | " | 1 |
| " | " | 5 | " | " | |
| " | " | 10 | " | " | |
| " | " | 20 | " | " | |
| " | " | 30 | " | " | |
| " | " | 15 | " | " | |
| " | " | 30 | " | " | |
| " | " | 60 | " | " | |
| " | " | 120 | " | " | |
| 20 | 90 | 30 | NaSCN | none | |
| 20 | 90 | 30 | TMS—NCS | " | |
| " | 50 | 90 | " | " | |
| " | 90 | 240 | " | " | |

1. Sample was evaporated prior to addition of acetic anhydride.

Preferably approximately two (2) nanomols of a peptide are included in ten (10) microliters of a solution containing the isothiocyanate to obtain a reaction which produces a high yield of peptidyl thiohydantoin derivative. This constitutes a distinct advantage over the prior art since an amount of peptides in the micromolar range has had to be used in the prior art to obtain any satisfactory results.

The peptide may be included in the solution in either a liquid phase or a solid phase. When the peptide is included in the solution in the solid phase, the solid phase support may precipitate in the solution but the peptide attached to the solid phase support may be considered as being effectively dissolved in the solution because it extends into the solution from the solid phase support in such a manner as to be positioned for reaction with the isothiocyanate in the solution. The use of a solid phase support for a peptide is well known in the art.

The reaction of the peptide and the isothiocyanate preferably occurs in a temperature range of approximately 50° C. to approximately 90° C. For example, when the reaction occurs at a temperature of approximately 90° C., a complete conversion of the peptide to a peptidyl thiohydantoin occurs in a period of time as short as thirty (30) minutes. The reaction of the peptide and the thiocyanate radical in the presence of acetic anhydride to obtain the peptidyl thiohydantoin derivative is shown in Equation 1.

Complete conversion of the peptide to a peptidyl thiohydantion derivative is also obtained at temperatures of approximately 70° C. and 50° C. However, the amount of time required to complete the conversion increases as the temperature of the solution is decreased. For example, a rate constant as shown in the table below has been obtained for the temperatures specified below:

| Temperature | Rate Constant | Inclusion of Catalyst |
| --- | --- | --- |
| 70° C. | $5 \times 10^{-4}$ | No |
| 70° C. | $2 \times 10^{-3}$ | Yes |
| 50° C. | $7 \times 10^{-5}$ | No |
| 50° C. | $6 \times 10^{-4}$ | Yes |

The above are in comparison to a rate constant of $4 \times 10^{-3}$ when the reaction occurs at a temperature of approximately 90° C. in the presence of a catalyst. The rate constant may be defined as the reciprocal of the rate at which the peptide is converted to the peptidyl thiohydantoin in the solution discussed above.

After a complete conversion of the peptide to the peptidyl thiohydantoin derivative has been obtained as discussed above, excess reagents (such as trimethylsilyl isothiocyanate) may be removed from the solution in a conventional manner as by extraction with a suitable solvent. This removal is facilitated if the peptide is initially immobilized by fixation to a solid support or entrapment within a matrix or retentive material, such as polybrene.

A suitable material such as hydrochloric acid is then added to the solution containing the peptidyl thiohydantoin derivative to cleave such derivative. The reaction may occur at ambient temperatures when the hydrochloric acid has a concentration such as approximately 12N. The chemical reaction producing the cleavage is shown schematically in Equation 2. As will be seen, this chemical reaction causes the thiohydantoin derivative of the amino acid at the carboxyl terminal of the peptidyl thiohydantoin derivative to be liberated. A peptide residue constituting the peptide minus the separated amino acid is also produced. The amino acid from which the thiohydantoin is derived can then be identified by conventional methods.

The method steps discussed above can be repeated to cleave and identify the amino acids at successive positions from the carboxyl terminal of the peptide or the peptidyl residue. The number of amino acids cleaved and identified in this manner may be as high as twenty five (25) or more, depending on the nature of the amino acids constituting the peptide. When it is desired to cleave and identify the amino acid in a peptide containing more than fifty (50) amino acids, an additional material such as hexafluoroacetone may be included in the solution containing the trimethylsilyl isothiocyanate to facilitate the sequencing of such peptides with such extended sequences of amino acids.

The methods described above have certain important advantages. One distinct advantage is that a complete conversion of the peptide of the peptidyl thiohydantoin derivative is obtained. This in turn provides for a complete cleavage of the peptidyl thiohydantoin derivative to obtain the thiohydantoin derivative of the amino acid initially at the carboxyl terminal of the peptide and to obtain the peptidyl residue. This facilitates the identification of the amino acid in the thiohydantoin derivative. It also maintains substantially the same relative molar concentration of the peptidyl residue as in the original peptide. As a result, the ease of identification of amino acids at subsequent positions of the peptidyl residue is enhanced. This is in contrast to methods of the prior art where portions of the peptidyl residue are removed for analysis to identify the deleted amino acid. Such methods progressively reduce, with each sequential removal of the amino acid from the carboxyl terminal, the quantity of the residual peptide available for the subsequent step. Furthermore, by maintaining the molar concentration of the peptidyl residue substantially constant with progressive sequencing of the amino acids at the carboxyl terminal of the peptidyl residue, the number of amino acids capable of being sequenced becomes considerably increased in comparison to the number of amino acids capable of being sequenced in the methods of the prior art.

The methods disclosed above also have other important advantages. The methods provide a complete conversion of the peptide to the peptidyl thiohydantoin derivative by using chemicals (and specifically trimethylsilyl isothiocyanate) which are quite reactive with peptides, but which are considerably more stable under ambient conditions than the materials now being used. However, it is desirable that the trimethylsilyl isothiocyanate should be isolated from water and water vapor since the trimethylsilyl isothiocyanate is reactive with water. The methods constituting this invention are also advantageous because they minimize the times and temperatures needed to convert the peptide substantially completely to the peptidyl thiohydantoin.

Materials and Methods

General. All distillations were performed under an inert atmosphere in a fume hood, and the distillates were stored in ampoules in the cold room (4° C.). Solvents were either reagent or liquid chromatography grade from J. T. Baker. Sodium thiocyanate, ammonium thiocyanate, trimethylsilyl isothiocyanate (TMS-NCS), trifluoromethane sufonic acid (TFMSA), acetohydroxamic acid and dimethylaminopyridine (DMAP), were purchased from Aldrich Chemical Co. Triethylamine was Pierce sequanol grade. Dimethylallylamine (DMAA) was obtained from Pierce. Acetic anhydride and acetic acid were distilled. Triflouroacetic acid (TFA) was distilled from chromium trioxide and then from alumina in a manner known in the prior art. Pyridine was distilled from calcium hydride. Bradykinin was obtained from Vega Biochemicals and was further purified using system A below. Water was passed through a Millipore Milli-Q system with the organic cartridges.

HPLC. Reverse-phase high performance liquid chromatography (HPLC) was performed on two LC systems. A Beckman model 344 gradient system with detection at 214 nm (Model 160 detector), or a Waters model 441 with detection at 214 nm was used for the peptide work. A Vydac C4 column, 214TP54 25×0.42 cm (The Separations Group) was employed for all peptide elutions. A DuPont 850 system was used for analysis of the thiohydantoins at 254 nm. The elution systems used were:

A. For peptides, solvent 1, 0.1% TFA in water. Solvent 2, 0.1% TFA, 90% acetonitrile, balance water.

B. For thiohydantoins, solvent 1, 15 mM TFA, 0.45 mM acetic acid, adjusted to pH 4.0 with 5.0N NaOH. Solvent 2, either 15 or 37 mM TFA in 90% acetonitrile, pH 3.4.

The columns used on the DuPont HPLC equipment with variations of system B were Econosphere C18 15×0.46 cm (Alltech Associates, Deerfield IL), and Ultrasphere ODS 15×0.46 cm, and 25×0.46 cm (Beckman/Altex). The separations were performed at room temperature and at a flowrate of 1.0 mL per minute.

The gradient profile used for peptides was a simple linear ramp from 0% to 60% solvent 2 over 60 minutes. A typical program for thiohydantoins was 0% to 50% solvent 2 in 20 minutes, then to 100% in 2 minutes. The low pressure mixing volume of the DuPont equipment provided an initial isocrat of about 5 minutes by default.

Mass Spectrometry. Spectra were run in either FAB (fast atom bombardment) or EI (electron impact) mode on a JEOL HX100HF mass spectrometer fitted with the standard Jeol FAB accessory. For the fast atom bombardment mode, a small amount of solid amino acid thiohydantoin (about 1 mg or less) was added to 2-3 $\mu$L of glycerol on the sample stage. Peptides were sampled directly, concentrated and then sampled, or dried down and redissolved in 10% acetic acid. One to three $\mu$l of liquid sample was applied to the stage. For the electron impact mode, the sample itself was not heated but was applied to the electron impact probe (a few $\mu$L of concentrated solution) and thrust into the heated (250° C.) source.

Preparation of Thiohydantoins. The procedure used was essentially a scaled down version disclosed by C. D. Cromwell and G. R. Stark in Biochemistry in 1969 at Volume 8, page 4735. One mmole of amino acid was weighed into a 13×100 mm glass tube, and dissolved in 1 to 2 mL of acetic anhydride-acetic acid about 4:1 v/v, with heating (90° C., heating block) and vortexing. After 10 to 40 minutes, 100 mg of NH4SCN or NaSCN was added, vortexed into solution and heated for 30 minutes. The reaction was cooled to room temperature and evaporated in a Savant vacuum centrifuge (no heat) under vacuum. Hydrolysis of the amino acid acetyl thiohydantoin was carried out in 1 to 2 mL of 12N HCl at room temperature for 30 minutes. Vortexing, and sometimes sonication, aided in redissolving the intermediate. The sample was evaporated to dryness in a vacuum centrifuge, and recrystallized from water, water-ethanol, or 95% ethanol. Samples were usually dissolved in water, ethanol-water or methanol-water for further analysis. Aliquots of the individual derivatives were combined to produce a standards mix for use in calibrating the HPLC columns to be used in identifying the amino acid thiohydantoins liberated in the sequencing operation.

Thiocyanate degradations. The solution phase degradations were conveniently carried out in 1.4 mL polypropylene tubes with caps. Thus, 10 $\mu$L of purified peptide (20 or 2 nmoles of bradykinin in HPLC buffer, from system A) was placed in a tube with 50 $\mu$L acetic anhydride. After heating (50° C. or 90° C.) for 5 to 10 minutes, reagent was added. The reagent was one of: 2 mg solid NaSCN, 25 $\mu$L of NaSCN dissolved in acetic anhydride (50 mg in 400 $\mu$L), or 5 $\mu$L of TMS-NCS. The standard reaction condition was 30 minutes at 90° C. unless otherwise specified. The reaction was either quenched with 50 $\mu$L of water, or not, and then evaporated to dryness. For analysis, the material was taken up in a volume of water (typically 50 $\mu$L or 100 $\mu$L), an aliquot taken and the balance evaporated again. The dried peptidyl thiohydantoin derivative was then subjected to 50 $\mu$L of 12N HCl for 30 minutes at room temperature to effectuate cleavage. After evaporation, the residue was again redissolved in water for further analysis.

To screen for possible catalysis, a standard TMS-NCS coupling (90° C.) was used, but for 10 minutes (see below), and one $\mu$L of either pyridine or neat TFMSA was added immediately prior to addition of the reagent. The TFMSA made an audible hiss when it was added. DMAP was dissolved in acetic anhydride at approximately the calculated molar concentration of the pyridine in the previous experiment. This solution was then used in place of acetic anhydride in the coupling. Cleavage again remained constant (12N HCl, 30 minutes, room temperature).

Cleavage with triethylamine was attempted by using TMS-NCS in a standard coupling as disclosed by J. L. Mueth, D. E. Harris, F. E. Dwulet, M. L. Crowl-Powers and F. R. Gurd in Biochemistry in 1982 at Volume 16, page 3750. Hence 50 $\mu$L of 2% triethylamine in water was added to the dry, coupled product. After 30 minutes at room temperature, the sample was evaporated in a Savant vacuum centrifuge (no heat) under vacuum, dissolved in water, and a portion analysed.

In a similar fashion, cleavage with acetohydroxamate was tried. After drying down the coupled product, 50 $\mu$L of 0.2M acetohydroxamate with a pH of 8.0 was added, vortexed and allowed to stand for 30 minutes at room temperature. Solvent was removed and the sample analysed.

Preliminary kinetic studies. Approximate kinetics were studied by varying the coupling time and/or temperature (see Table 3), while holding the cleavage conditions constant (also see Table 3). The final products only were then analysed by HPLC. In one experiment, timepoints of 15, 30, 60, and 120 minutes at 90° C. were run, unquenched (see Table 3), using otherwise standard coupling conditions and TMS-NCS. Similarly, another experiment examined shorter times: 5, 10, 20, and 30 minutes at 90° C., but with quenching. At 50° C., only a 90 minute experiment was run.

The effect of pyridine was observed (see Table 3) at 90° C. for 10 minutes, and at 50° C. for 15 and 30 minutes. TFMSA and DMAP were examined at 90° C. for 10 minutes. Rate constants were calculated from single time points assuming pseudo first-order kinetics.

The Amino Acid Thiohydantoins

A complete discussion occurs in the article by Cromwell and Stark in the 1969 issue of Biochemistry. Although they describe the preparation at the 10 mmole level, applicant has found the 1 mmole scale to be convenient, allowing the reactions to be carried out in common 13×100 mm tubes. This makes the procedure compatible with standard laboratory equipment: vortex mixer, heating block, and Savant speed-vac vacuum centrifuge.

Individual amino acid thiohydantoins were prepared as indicated. All products were characterized by HPLC and by electron impact mass spectrometry. Some were also characterized by fast atom bombardment mass spectrometry. The fast atom bombardment spectra were complicated by matrix ions, so the electron impact method was found to be generally more suitable for these compounds. In general the spectra were in good agreement with data pulished by T. Suzuki, K. D. Song, Yi Itagaki and K. Tagimura in Organic Mass Spectrometry in 1976 at Volume II, Page 557. Most of the thiohydantoins exhibited a single peak on HPLC with notable exceptions, serine being a prime example in applicant's method as in other methods of the prior art.

Three (3) of the non-polar amino acids (phenylalanine, tyrosine, and isoleucine) contained quantities of the respective acetyl-thiohydantoins from incomplete cleavage, probably due to low water solubility, but the problem was not serious. Samples of tryptophan triohydantoin contained hydrophobic impurities by HPLC analysis. It is recommended that such samples be purified by HPLC. Several amino acids are difficult to purify by crystallization, including histidine (H), asparagine (N), glutamine (Q), lysine (K), arginine (R), glutamic acid (E), and aspartic acid (D). HPLC is again suggested for purification. Material isolated from preparations involving aspartic acid and glutamic acid were not identifiable as thiohydantoins by the mass spectrometer. When analyzed, the mother liquor of the glutamic acid reaction mixture did exhibit an ion at 188, expected for the glutamic acid thiohydantoin. Apparently a byproduct crystallizes in preference to the desired product. The mother liquors from the reaction with aspartic acid have not yet been further studied. A sample precipitated from a coupling with proline did not give the expected ion and was not further investigated. Reaction of carboxymethylcysteine was not studied. An improved procedure for aspartic and glutamic thiohydantoins has been reported in the above cited paper by Suzuki et al. It would be expected to succeed for carboxymethylcysteine also.

A partial standards mix was prepared to develop an analytical separation. HPLC has been used to separate the thiohydantoins (see article by J. L. Meuth, D. E. Harris, F. E. Dwulet, M. L. Crowl-Powers and F. R. Gurd in Biochemistry in 1982 at Volume 16, page 3750) but the separation of all the derivatives in a single run has not been shown. This resembles the state in which HPLC separations of PTH-amino acids existed a few years ago.

The Thiocyanate Degradation

Applicant's basic strategy was to concentrate his efforts on a single simple model system in which a complete characterization of the degradation might be possible. Bradykinin (arginyl propyl propyl glycyl phenylalanyl seryl prolyl phenylalanyl argine) (RPPGFSPFR) was selected as the model peptide because it is easily purified by HPLC, has arginine at the C-terminus (as many tryptic peptides do), has a reasonable mass and is readily available. Applicant has used bradykinin as an amino-terminal sequence standard as well. The plan was to isolate both the coupling and cleavage reaction products and study them by fast atom bombardment mass spectrometry. This approach should enable the detailed study of side reactions at the carboxyl terminal or reactive side chain residues, information not easily gained by other techniques.

The reaction was first studied at the 20 nmole level to ensure sufficient material for both analytical and small preparative HPLC runs. The liquid chromatography profile of an aliquot of the coupling reaction with NaSCN was monitored at 214 nm. The balance of this experiment was cleaved with HCl and then run preparatively on HPLC. The fast atom bombardment mass spectrometry of the products showed the 2 major peaks to be N-acetyl des-arg bradyinin, the expected peptide. The reason for this peak splitting is not clear. The next major peptide peak was assigned as N-acetyl-bradykinin, i.e. recovered starting material, and gave the correct molecular ion. The other two major peaks analysed appeared to be non-peptide byproducts, perhaps thiocyanate polymer.

The other popular reagents have been HSCN (see the article by J. L. Meuth et. al. in the 1982 issue of Biochemistry) and other salts (usually ammonium, but rarely potassium). There is little, if any, reason to expect these salt solutions to be more stable than the sodium salt, and the acid is well known to be unstable. Possibly the higher ionic strength of the salts is related to the deficiencies of these reagents but would not be a problem with the free acid. This explains the superiority of the acid. Another commercially available isothiocyanate is the trimethylsilyl (TMS) derivative. This compound was interesting because it sould be reasonably stable (except hydrolytically). In fact, the material is stored and shipped without refrigeration, so thermal stability is not a problem. It was found to be sufficiently reactive to be useful.

The reaction with TMS-NCS was carried out very similarly to the NaSCN reaction. A chromatogram of the product after HCl was exceptionally clean. It showed a peak to be N-acetyl-des arg bradyinin, obviously the major product. The reagent blank and thiohydantoin chromatograms are also uncomplicated, compared with the other reactions studied. For this reason, TMS-NCS was used to establish advantageous reaction conditions.

The potential for catalysis was investigated. In Biochemistry in 1968 at Volume 1, Page 1796, G. R. Stark discussed the possible involvement of general base catalysis in the coupling. He showed data for amino acids and a short peptide adding sodium acetate to the medium, but the idea did not receive popular support. Although he did not report rate constants, pseudo first-order rate constants can be calculated from his data. The caveat was that reaction with larger peptides was purported to be much slower under these conditions, but no data was offered to illustrate this point. In an article in Peptide Protein Research in 1979 at Volume 13, Page 122, Dwulet and Gurd offered rate constants for HSCN with proteins and invoked a solvent effect to explain the reactivity of their reagent.

To assess the kinetics, the reaction time was varied at the 2 nmole level at 50° C. and 90° C. The sample was coupled, water quenched, cleaved and then analyzed for peptide products. Without quenching, the reaction might continue during the evaporation. (This was shown to affect the product distribution). Applicant studied the reaction at 5, 10, 20 and 30 minutes. Comparing the 20 and 30 minute chromatograms suggests that some decomposition may occur at longer reaction times. It was therefore desirable to reduce the severity of reaction conditions if possible.

The 10 minute time point was chosen to screen for catalysis because the reaction is approximately 50% complete then, so both starting material and product are easily detected. Any difference in rate should be readily apparent. Pyridine was added to one reaction and TFMSA to another, and a control run was made simultaneously (standard conditions, no additives). The TFMSA reaction appeared to give no peptide products and was not further pursued. The pyridine reaction, however, showed a significant increase in the ratio of product to starting material. In fact, the reaction appears to be essentially complete. At 50° C., the reaction without pyridine proceeds to about 20 to 30% completion (estimated) in 90 minutes, an unacceptable rate to achieve reasonable cycle times. In the presence of pyridine, however, the half life is about 12 minutes. The pseudo first-order rate constants calculated from these data indicate apparent rate enhancements of a factor of 4.5 to 90° C. and about 8 at 50° C.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In a method for sequencing a peptide by carboxyl terminal degradation which comprises coupling the carboxyl terminus of a peptide with a coupling reagent to form a peptidyl thiohydantoin derivative, cleaving the peptidyl thiohydantoin derivative to provide a thiohydantoin derivative of the amino acid previously at the carboxyl terminus of the peptide and a peptidyl residue lacking such an amino acid, and identifying the amino acid in the amino acid thiohydantoin derivative, wherein the improvement comrprises utilizing a silyl isothiocyanate as the coupling reagent.

2. The method of claim 1 in which the isothiocyanate has the formula $R_{(x)}Si(NCS)_y$ where x is 0 to 3, y is 1 to 4 and R is an alkyl or an aryl substituent.

3. The method of claim 2 in which the isothiocyanate is trimethylsilyl isothiocyanate.

4. The method of claim 2 in which a catalyst is included in the coupling reagent.

5. The method of claim 4 in which the catalyst is a tertiary amine.

6. The method of claim 4 in which the catalyst is pyridine.

7. The method of claim 2 in which a weak organic acid anhydride is included in the coupling reagent.

8. The method of claim 7 in which the weak organic acid anhydride is acetic anhydride.

* * * * *

UNITED STATES PATENT AND TRADEMARK OFFICE
CERTIFICATE OF CORRECTION

PATENT NO. :  4,837,165
DATED      :  June 6, 1989
INVENTOR(S):  David H. Hawke

It is certified that error appears in the above-identified patent and that said Letters Patent is hereby corrected as shown below:

Column 1, line 5, after the title, insert:

--This invention was made with government support under Grant No. CA33572 awarded by the National Institutes of Health. The government has certain rights in the invention.--

Signed and Sealed this

Second Day of April, 1996

Attest:

BRUCE LEHMAN

Attesting Officer

Commissioner of Patents and Trademarks